(12) United States Patent
Rosenbloom

(10) Patent No.: US 7,396,546 B2
(45) Date of Patent: *Jul. 8, 2008

(54) ANTI-MICROBIAL COMPOSITIONS AND METHODS OF USING SAME

(75) Inventor: Richard A. Rosenbloom, Elkins Park, PA (US)

(73) Assignee: The Quigley Corporation, Doylestown, PA (US)

( * ) Notice: Subject to any disclaimer, the term of this patent is extended or adjusted under 35 U.S.C. 154(b) by 129 days.

This patent is subject to a terminal disclaimer.

(21) Appl. No.: 10/359,889

(22) Filed: Feb. 6, 2003

(65) Prior Publication Data

US 2003/0185912 A1 Oct. 2, 2003

Related U.S. Application Data

(63) Continuation-in-part of application No. PCT/US02/24794, filed on Aug. 6, 2002, which is a continuation-in-part of application No. 10/122,991, filed on Apr. 15, 2002, now Pat. No. 6,596,313, which is a continuation-in-part of application No. 09/923,090, filed on Aug. 6, 2001, now Pat. No. 6,592,896.

(51) Int. Cl.
*A61K 36/82* (2006.01)
*A61K 9/20* (2006.01)

(52) U.S. Cl. .................. 424/729; 424/756; 424/464; 424/440; 424/451; 424/441; 424/489

(58) Field of Classification Search ............... 424/464, 424/451, 48, 441, 440, 434, 435
See application file for complete search history.

(56) References Cited

U.S. PATENT DOCUMENTS

| | | | |
|---|---|---|---|
| 4,592,912 A * | 6/1986 | Nickolaus | 424/748 |
| 5,120,538 A | 6/1992 | Oei | |
| 5,137,922 A * | 8/1992 | Shimamura et al. | 514/731 |
| 5,248,504 A | 9/1993 | Friedman | |
| 5,385,734 A | 1/1995 | Friedman | |
| 5,401,504 A | 3/1995 | Das et al. | |
| 5,494,668 A | 2/1996 | Patwardhan | |
| 5,707,630 A | 1/1998 | Morrow | |
| 5,804,603 A * | 9/1998 | Chen | 514/630 |
| 5,861,415 A | 1/1999 | Majeed et al. | |
| 5,908,857 A | 6/1999 | Suzuki | |
| 6,030,980 A | 2/2000 | Suzuki | |
| 6,063,381 A | 5/2000 | Staggs | |
| 6,174,542 B1 | 1/2001 | Hinton et al. | |
| 6,261,607 B1 | 7/2001 | Newmark et al. | |
| 6,264,995 B1 * | 7/2001 | Newmark et al. | 424/725 |
| 6,274,177 B1 | 8/2001 | Wu et al. | |
| 6,291,533 B1 * | 9/2001 | Fleischner | 514/682 |
| 6,391,346 B1 | 5/2002 | Newmark et al. | |
| 6,399,105 B1 * | 6/2002 | Collin | 424/550 |
| 6,596,313 B2 * | 7/2003 | Rosenbloom | 424/464 |
| 6,827,945 B2 * | 12/2004 | Rosenbloom | 424/464 |
| 6,841,544 B2 * | 1/2005 | Gelber et al. | 514/54 |

FOREIGN PATENT DOCUMENTS

| | | | |
|---|---|---|---|
| CN | 1060012 A | * | 4/1992 |
| CN | 1072823 A | * | 6/1993 |
| CN | 1116068 A | * | 2/1996 |
| JP | 2000157209 A | * | 6/2000 |
| WO | WO 99/37314 | * | 7/1999 |

OTHER PUBLICATIONS

PDR for Herbal Medicine: 1st edition 1998, 661-662-786-787-1196.*
Besselaar et al. Impact of the introduction of A/Sydney/5/97 H3N2 influenza virus into South Africa. J Med Virol. Dec. 1999; 59(4):561-8.*
Internet download, Prinz et al., "Saliva Tannin interactions", *J. Oral Rehabil*, Nov. 2000; 27(11) :991-4.
Internet download; Bacon et al., "Binding affinity of hydrolysable tannins to parotid saliva and to proline-rich proteins derived form it", *J. Agric Food Chem* Mar. 2000; 48(3) : 838-43.
Internet download; Lomniczi et al., "Inhibition of salivary secretion by lipopolysaccharide: possible role of prostaglandins", *Am J. Physiol Endocrinol Metabm* Aug. 2001; 281.
Internet download; Brouet et al., "Curcumin an anti-tumour promoter and anti-inflammatory agent, inhibits induction of nitric oxide synthase in activated macrophages". *Biochem Biophys Res Commun* 1995 Jan. 17; 206.
Internet download, Rettori et al., "Control of salivary secretion by nitric oxide and its role in neuroimmunomodulation", *Ann NY Acad Sci* 2000; 917:258-67.
Internet download, Tjendraputra et al., "Effect of Ginger Constituents and Synthetic Analogues on Cyclooxygenase-2 Enzyme in Intact Cells", *Bioorg Chem* Jun. 2001;29(3):156-163.
Internet article; ALS Survival Guide, Treatment for ALS; Feb. 5, 2002, pp. 1-15; lougehrigsdisease.net/als.

(Continued)

*Primary Examiner*—Michael G. Hartley
*Assistant Examiner*—Jake M. Vu
(74) *Attorney, Agent, or Firm*—Knoble, Yoshida & Dunleavy LLC

(57) ABSTRACT

An anti-microbial composition is provided. The anti-microbial composition includes a first ingredient obtainable from ginger, a second ingredient obtainable from green tea, an optional third ingredient available from turmeric, and, optionally, an acceptable carrier. Also provided are methods of reducing, treating or preventing at least one symptom or adverse effect of microbial infection in a patient. The methods include the step of administering to the patient prior to expected exposure to a microbe, concurrently with exposure to a microbe, or after exposure to a microbe, an effective amount of a composition of the invention.

21 Claims, No Drawings

OTHER PUBLICATIONS

Park, Sialorrhea, "The Drooling Patient", Loyola University Health System, The Department of Otolaryngology Head & Neck Surgery, pp. 1-3, luhs.org/depts./otolryn/P_peds1.htm.

Salzer, "Sialorrhea", Grand Rounds Archive at Baylor, The Bobby r. Alford Department of Otorhinolaryngology and Communicative Sciences, 1-3.

Rettori et al., "Control of Salivary secretion by nitric oxide and its role in neuroimmunomodulation", Ann NY Acad Sci 2000;917:258-67.

Mier et al., "Treatment of Sialorrhea with glycopyrrolate A Double-blind, Dose-Ranging Study", Pediatrics & Adolescent Medicine, vol. 154, No. 12, Dec. 2000.

Internet page, "Where are your salivary glands?",.cfm American Academy of Otolaryngology—Head and Neck Surgery, entnet.org/healthinfo/throat/salivary.

Legeza, et al., "Prostaglandins—their role in the mechanisms of the development of the primary reaction to radiation syndrome", Radiats Biol Radioecol Jan.-Feb. 1994;34(1):32-8.

Novozhenov, et al., "Changes in lipid peroxidation and the antioxidant system in patients with acute radiation sickness", Voen Med Zh Apr. 1993;(4):38-40, 80 Abstract.

Chaialo, et al., "Free-radical processes and blood antioxidant systems in the late period following acute radiation sickness", Med Radiol (Mosk) 1991;36(5):20-1 Abstract.

Legeza, et al., "Prostaglandins—their role in the mechanisms of the development of the primary reaction to radiation syndrome", Radiats Biol Radioecol Jan.-Feb. 1994;34(1):32-8.

Bazhan, "Lipid peroxidation and the antioxidant system in subjects exposed to the influence of extreme factors", Lik Sprava Dec. 1998;(8):47-50 Abstract.

Beckman, et al., "Radiation therapy impairs endothelium-dependent vasodilation in humans", J Am Coll Cardiol Mar. 2001;37(3):761 Abstract.

Castillo, et al., "Antiosidant activity and radioprotective effects against chromosomal damage induced in vivo by X-rays of flavan-3-ols (Procyanidins) from grape seeds (Vitis vinifera): comparative study versus other phenolic and organic compounds", J Agric Food Chem May 2000;48(5):1738-45 Abstract.

Weiss, et al., "Radioprotection by antioxidants", Ann N Y Acad Sci 2000;899:44-60 Abstract.

Weiss, "Pharmacologic approaches to protection against radiation-induced lethality and other damage", Environ Health Perspect Dec, 1997;105 Suppl6:1473-8 Abstract.

Baraboi, et al., "Mechanism of the antistressor and antiradiation action of plant phenol compounds", Ukr Biokhim Zh Nov.-Dec. 1998;70(6):13-23 Abstract.

Wu, et al., "Synthesis and bio-activity of coumarin derivatives and studies on its relationships between activity and lipophilicity", Yao Xue Xue Bao 1993;28(4):266-72 Abstract.

Thresiamma, et al., "Protective effect of curcumin, ellagic acid and bixin on radiation induced toxicity", Indian J Exp Biol Sep. 1996;34(9):845-7 Abstract.

Deneke, "Thiol-based antioxidants", Curr Top Celll Regul 2000;36:151-80 Abstract.

Il'iuchenok, et al., "Pharmacological and radioprotective properties of some gamma-pyrone derivatives (flavanones and flavanols)", Farmakol Toksikol Sep.-Oct. 1975;38(5):607-12.

Kapitanov, et al., "Radiation-protective effectiveness of lycopene", Radiats Biol Radioecol May-Jun. 1994;34 (3):439-45 Abstract.

Beliaev, et al., "Modification of the body's resistanct to acute ionizing radiationby synthetic beta-carotene", Vopr Med Khim Nov.-Dec. 1992;38(6):39-42 Abstract.

Chigareva, et al., "Radio-protective effect of sulfur-containing methylfuran derivatives and the role of thiols in its realization", Radiobiologiia Nov.-Dec. 1983;23(6):816-9 Abstract.

Samoilov, et al., "The radioprotective and antioxidant properties of solubilized alpha-tocopheraol acetate", Eksp Klim Farmakol Jul.-Aug. 1992;55(4):42-4 Abstract.

Kamat, et al., "Chlorophyllin as an effective antioxidant against membrane damage in vitor and ex vivo", Biochim Biophys Acta Sep. 27, 2000;1487(2-3):113-27 Abstract.

Internet download, "1001 Herbs for a Healthy Life" 2001, 1001 Herbs; pp. 1 and 2.

Internet download, "Slippery Elm", MotherNature.com Health Encyclopedia, 1995-2000, MotherNature.com Inc., pp. 1 and 2.

Uma, et al., "Radiation protection by the ocimum flavonoids orientin and vicenin: mechanisms of action", Radiat Res Oct. 2000; 154(4):455-60 Abstract.

Moskalenko, et al., "The role of immunological mechanisms in the development of the late sequelae of nuclear disasters", Lik Sprava Jun. 1999;(4):3-8 Abstract.

Ovsiannikova, et al., "Efficacy of antioxidant preparations used for correction of impairment of oxidative homeostasis in Chernobyl liquidators", Radiats Biol Radioecol Mar.-Jun. 1999;39(2-3):318-21, Abstract.

Spector, et al., "Reduction of x-radiation mortality by cabbage and broccoli", Proceedings of the Society of Experimental Biology and Medicine 100:405-407 Citation.

Calloway, et al., "Further studies of the influence of diet on radiosensitivity of guinea pigs, with special reference to broccoli and alfalfa", Journal of Nutrition 19:34o-348 Citation.

Chlorophyll as Therapy; 4:1-5; www.wheatgrass.com/book/chapter4.html.

Gamma Ray Irradiation; "Research finds chorella may offer protection against gamma-ray irradiation", www.health-books.com/PressRoom/Gamma.html; 1-2.

Antioxidants; "Also Known as: Free Radical Scavengers; Oxidative Scavengers", www.alternativehealth.com.au/antioxid.html; 1-9.

Goodman, "Protection From Heavy Metal and Radiation Poisoning", Germanium-The health and life enhancer, 5:1-8.

A fanas'ev, et al., "Chelating and free radical scavenging mechanisms of inhibitory action of rutin and quercetin in lipid peroxidation", Biochem Pharmacol Jun. 1, 1989;38(11):1763-9 Abstract.

Ishige, et al., "Flavonoids protect neuronal cells from oxidative stress by three distinct mechanisms", Free Radic Biol Med Feb. 15, 2001;30(4):433-46 Abstract.

Shobana, et al., "Antioxidant activity of selected Indian spices", Prostaglandins Leukot Essent Fatty Acids Feb. 2000;62(2):107-10 Abstract.

Tiukavkina, et al., "Dihydorquercetin—anew antioxidant and biologically active food additive", Vopr Pitan 1997;(6):12-5 Abstract.

Plumb, et al., "Antioxidant properties of flavonal glycosides from tea", Redox Rep 1999;4(1-2):13-6 Abstract.

Skaper, et al., "Quercetin protects cutaneous tissue-associated cell types including sensory neurons from oxidative stress induced by glutathione depletion: cooperative effects of ascorbic acid", Free Radic Biol Med 1997;22(4):669-78 Abstract.

Jones, et al., "Radioprotective effect of free radical scavenging enzymes", J Otolaryngol Oct. 1990;19(5):299-306 Abstract.

Boloor, et al., "Chlorophyllin as a protector of mitochondrial membranes against gamma-radiation and photosensitization", Toxicology Nov. 30, 2000;155(1-3):63-71 Abstract.

Kim, et al, "In vivo radioprotective activity of Panax ginseng and diethyldithiocarbamate", In Vivo Sep.-Oct. 1993;7(5):467-70 Abstract.

Rice-Evans, et al., "The relative antioxdant activities of plant-derived polyphenolic flavonoids", Free Radic Res 22:4:375-83 1995 Summary.

Gillis, "Panax ginseng pharmacology: a nitric oxide link", Biochemical Pharmacology 54:1-8 (1997) Summary.

Duke, et al., "Biological Activities of Curcuminoids", Phytochemical and Ethnobotanical Database.

Robak, et al., "Bioactivity of flavonoids", Pol J Pharmacol Nov.-Dec. 1996;48(6):555-64 Abstract.

Bursel, et al., "Can protein kinase C inhibition and vitamin E prevent the development of diabetic vascular complications?", Diabetes Res Clin Pract Sep. 1999;45(2-3):169-82 Abstract.

Freedman, et al., "Select flavonoids and whole juice from purple grapes inhibit platelet functionand enhance nitric oxide release", Circulation Jun. 12, 2001;103(23):2792-8 Abstract.

Lin, et al., "Recent studies on the biofunctions and biotransformations of curcumin", Biofactors 2000;13(1-4):153-8 Abstract.

Isoherranen, et al., "Ultraviolet irradiation induces cyclooxygenase-2 expression in keratinocytes", *Br J Dermatol* Jun. 1999;140(6):1017-22 Abstract.

Duarte, et al., "Vasodilator effects of quercetin in isolated rat vascular smooth muscle", *Eur J Pharmacol* Aug. 1993 239:1-7 Abstract.

Giugliano, et al., "Oxidative stress and diabetic vascular complications", *Diabetes Care* Mar. 1996;19(3):257-67 Abstract.

On, et al., "Vitamin c prevents radiation-induced endothelium-dependent vasomotor dysfunction and de-endothelialization by inhibiting oxidative damage in the rat", *Clin Exp Pharmacol Physiol* Oct. 2001;28(10):816-21 Abstract.

Konopacka, et al., "Modifying effect of vitamins C, E and beta-carotene agaist gamma-ray-induced DNA damage in mouse cells", *Mutat Res* Sep. 11, 1998;417(203):85-94 Abstract.

Shope, "Radiation-induced skin injuries from fluoroscopy", Scientific Exhibit 060PH at the 81st Scientific Assembly and Annual Meting of the Radiological Society of North America, Nov. 26-Dec. 1, 1995, Radiology vol. 197(P) Supplement, P449 Abstract.

Noble-Adams, "Radiation-induced skin reactions. 2: Development of a measurement tool", Br J Nurs Oct. 14-17, 1999;8(18):1208-11 Abstract.

Noble-Adams, "Radiation-induced skin reactions. 3: Evaluating in RISRAS", *Br J Nurs* Oct. 28-Nov 10, 1999;8(19):1305-12 Abstract.

Cusma, et al., "Real-time measurement of radiation exposure to patients during diagnostic coronary angiography and percutaneous interventional procedures", *J Am Coll Cardiol* Feb. 1999;33(2):427-35 Abstract.

DOE Openness: Human Radiation Experiments: Roadmap to the Project, ACHRE Report, "How Does Radiation Affect Humans", pp. 1-5 at http://tis.eh.doe.gov/ohre/roadmap/achre/intro.

DOE Openness: Human Radiation Experiments: Roadmap to the Project, ACHRE Report, "What is Ionizing Radiation?", pp. 1-3 at http://tis.eh.doe.gov/ohre/roadmap/achre/intro.

Newall et al., "The control of oral secretions in bulbar ALS/MND", *J. Neurol Sci*, Aug. 1996 vol. 139 Supp;:43-44.

Morgan et al., "Topical treatment of radiation induced dermatitis with N-acetylcysteine (NAC)(Meeting Abstract)", *Proc Annu Meet Am Assoc Cancer Res*, 1996; 37:A4142.

William F. Dial, *Cosmetic Dermatology*, "Topical Vitamin C May Help Protect Skin From UV Damage", Dec. 1991, pp. 34-35.

Bernard Idson, College of Pharmacy, University of Texas at Austin, Ultraviolet Irradiation Injury and Repair, Jan. 1992, pp. 22-24 and pp. 81-81.

Bissett et al., J. Soc. Cosmet. Chem., "Protective effect of a topically applied anti-oxidant plus an anti-inflammary agent against ultraviolet radiation-induced chronic skindamage in the hairless mouse", 43, Mar./Apr. 1992, pp. 85-92.

Darr et al., *"British Journal of Dermatology,"* Topical vitamin C protects porcine skin from ultraviolet radiation-induced damage (1992) 127, 247-253.

*Dermatology Times*, " New Aqueous Vitamin C blocks UV rays" 1991.

Fuchs et al., "Acute Effects of Near Ultraviolet and Visible Light on the Cutaneous Antioxidant Defense System" Oct. 3, 1988, pp. 739-744.

Vitamin E (Tocopherol) vs. Vitamin E Acetate, Roche, Jun. 1991.

Schmuth, et al., "Permeability barrier function of skin exposed to ionizing radiation" Arch Dermatol Aug. 2001; 137(8);1019-23.

Katiyar, et al., "Green tea polyphenol (-)-epigallocatechin-3-gallate treatment of human skin inhibits ultraviolet radiation-induced oxidative stress" Carcinogenesis Feb. 2001; 22(2):287-94.

Vitamin D-3 400 I.U.—The Way Up (http://www.thewayup.com/products/0028.htm).

* cited by examiner

ANTI-MICROBIAL COMPOSITIONS AND METHODS OF USING SAME

RELATED APPLICATION DATA

This application is a continuation-in-part of International patent application no. PCT/US02/24794, filed on Aug. 6, 2002, designating the United States of America and published in English; which, in turn, is a continuation-in-part of U.S. patent application Ser. No. 10/122,991, filed on Apr. 15, 2002 now U.S. Pat. No. 6,596,313, which, in turn, is a continuation-in-part of U.S. patent application Ser. No. 09/923,090, filed on Aug. 6, 2001 now U.S. Pat. No. 6,592,896.

BACKGROUND OF THE INVENTION

A. Field of the Invention

The present invention relates to anti-microbial compositions and methods of using them. More particularly, the present invention relates to anti-microbial compositions useful for treating one or more adverse effects of microbial infections, and to methods for administering the anti-microbial compositions.

B. Description of the Prior Art

Treatment of Microbial Infections

The medical literature regarding anti-microbial agents is vast and describes a number of anti-microbials including naturally occurring compounds as well as synthetic or semi-synthetic compounds produced in the laboratory. Consumers today often prefer to use naturally occurring compounds when these are available. Due to concern over side effects, which may be well documented side effects that occur in conjunction with a treatment, or possibly unknown side effects that may result from long-term use of a treatment, many consumers especially prefer anti-microbial treatments that are prepared from natural materials, such as herbs, with a minimal amount of chemical processing.

Treatment of Inflammation

Inflammation can result from microbial infections. In modern non-herbal medicine, there are two major categories of anti-inflammatory medicines: steroidal and non-steroidal. Steroidal anti-inflammatory medicines are powerful medications, which are based on hormonal substances, such as cortisone. Steroidal medications have a stronger anti-inflammatory response than non-steroidal medicines. Steroidal medications can be taken as pills, injected into the bloodstream, or injected directly into a joint space. There are many non-steroidal anti-inflammatory medications. Acetaminophen, aspirin, ibuprofen, and naproxen are the most commonly used non-steroidal anti-inflammatory medications.

Non-steroidal anti-inflammatory drugs have three major actions, all of which are related to inhibition of cyclo-oxygenase resulting in decreased formation of prostanoids. Firstly, an anti-inflammatory action can be achieved by reducing production of vasodilator prostaglandins (PGE2, PGI2), which means less vasodilation and, indirectly less oedema. Secondly, an analgesic effect can be achieved by reduced prostaglandin production (less sensitization of nociceptic nerve endings to the inflammatory mediators bradykinin and 5-hydroxytryptamine). Thirdly, an antipyretic effect can produce an anti-inflammatory action, probably due to a decrease in the mediator PGE2 generated in response to inflammatory pyrogens, much as interleukin-1.

There are side effects to both of these groups of medicines. They may include, among other things, stomach upset, stomach bleeding, or ulcers, kidney problems, hearing problems and ankle swelling. Additionally, the steroidal anti-inflammatory medications can have more serious side effects including: loss of bone mass, cataracts, reduced ability to fight infection, swelling and weight gain, mood changes, high blood pressure, and problems with the bone marrow where blood cells are produced.

It is therefore an object of certain embodiments of the present invention to provide an anti-microbial composition.

It is a further object of certain embodiments of the present invention to provide an anti-microbial composition made from natural products.

It is a still further object of certain embodiments of the present invention to provide a method for treating microbial infections by administering an anti-microbial composition.

It is a still further object of certain embodiments of the present invention to provide a method to treat microbial infections by administering a composition made from natural products.

These and other objects of the present invention will be apparent from the summary and detailed description of the invention, which follow.

SUMMARY OF THE INVENTION

In a first aspect, the invention provides an anti-microbial composition comprising a first ingredient obtainable from ginger, a second ingredient obtainable from green tea, and, optionally, an acceptable carrier, wherein the first ingredient is present in the anti-microbial composition in an amount effective to reduce, treat or prevent an adverse effect of microbial infection when administered to a patient prior to expected exposure to a microbe, concurrently with exposure to a microbe, or after exposure to a microbe.

In a further aspect the invention provides a method for the reduction, treatment or prevention of at least one adverse effect of microbial infection in a patient, comprising the step of administering to the patient prior to expected exposure to a microbe, concurrently with exposure to a microbe, or after exposure to a microbe, an amount of a composition comprising a first ingredient obtainable from ginger, a second ingredient obtainable from green tea, and, optionally, an acceptable carrier. The composition is effective, when administered, to reduce, treat or prevent an adverse effect of microbial infection in the patient.

DETAILED DESCRIPTION OF THE PREFERRED EMBODIMENTS

In a first aspect, the present invention relates to an anti-microbial composition. The anti-microbial composition of the present invention includes ingredients that can be obtained from ginger and green tea.

As used herein the term "flavors" includes both fruit and botanical flavors.

As used herein the term "sweeteners" includes sugars, for example, glucose, sucrose and fructose. Sugars also include high fructose corn syrup solids, invert sugar, sugar alcohols including sorbitol, and mixtures thereof. Artificial sweeteners are also included within the scope of the term, "sweetener."

As used herein, the term "acceptable" means a component that is suitable for use with humans and/or animals without undue adverse side effects (such as toxicity, irritation, and allergic responses), commensurate with a reasonable risk/benefit ratio.

Further, as used herein, the term "safe and effective amount" refers to the quantity of a component, which is sufficient to yield a desired therapeutic response without undue adverse side effects (such as toxicity, irritation, or allergic responses), commensurate with a reasonable risk/benefit ratio when used in the manner described herein.

The term "inhibiting" a microbe, as used herein, is meant reducing or preventing further growth of the microbe, and/or the elimination of some or all of the microbe from the human or animal being treated. Suitable methods for determining microbe inhibition are discussed in the examples.

All active compounds used in the present invention may be obtained from other sources, if available. Thus, the phrase "which can be obtained from" or the phrase "which may be obtained from" is meant to encompass compounds or compositions that are obtainable from turmeric, ginger, or green tea, and therefore encompasses synthetic forms of the same compounds and/or compositions as well as the same compounds and/or compositions obtained from other sources.

Most preferably, the anti-microbial composition of the present invention includes a first ingredient obtainable from ginger and a second ingredient obtainable from green tea, in a safe and effective amount to provide one or more of the beneficial effects described herein.

The first ingredient of the anti-microbial composition of the present invention may be obtained from ginger (*Zingiber officinale*, also commonly called ginger root). Native to southern Asia, ginger is a 2- to 4-foot perennial that produces grass-like leaves up to a foot long and almost an inch wide. Ginger root, as it is called in the grocery store, actually consists of the underground stem of the plant, with its bark-like outer covering scraped off.

Chinese medical texts from the fourth century B.C.E. suggest that ginger is effective in treating nausea, diarrhea, stomachaches, cholera, toothaches, bleeding, and rheumatism. Ginger was later used by Chinese herbalists to treat a variety of respiratory conditions, including coughs and the early stages of colds.

Ginger's modern use dates back to the early 1880s, when a scientist named D. Mowrey noticed that ginger-filled capsules reduced his nausea during an episode of flu. Inspired by this, he performed the first double-blind study of ginger. Germany's Commission E subsequently approved ginger as a treatment for indigestion and motion sickness. Ginger has become widely accepted as a treatment for nausea. Even some conventional medical texts suggest ginger for the treatment of the nausea and vomiting of pregnancy, although others are more cautious.

Ginger gives relief from muscular discomfort and pain. It inhibits prostaglandin and leukotriene biosynthesis and histamine release. Thus it acts as an anti-inflammatory as well as an antacid agent. It is a dual inhibitor of the lipoxigenase and cycloxigenase system. Ginger contains about 1 to about 4% essential oil (oleoresin). Used alone fresh Ginger is required to be used in substantially high doses (about 50 grams daily), which is not only inconvenient but can act as an irritant to the gastric mucosa. In dry form for any significant results, about 7 to about 10 grams of dry ginger powder has to be taken daily. Such large doses of ginger are extremely inconvenient for the patient and affect patient compliance on a daily basis. (See Potwardhan, U.S. Pat. No. 5,494,668.).

Ginger inhibits prostanoid synthesis and also products of 5-lipoxygenase. The potency of the ginger extract in the acute inflammation test appears to be comparable to that exhibited by acetyl salicylic acid reported in the same study. (Mascolo N. et al *Journal of Ethnopharmocology*, 1989, 27, 129-140).

One of the features of inflammation is increased oxygenation of arachidonic acid, which is metabolized by two enzymic pathways—the cyclooxygenase (CO) and the 5-lipoxygenase (5-LO)-leading to the production of prostaglandins and leukotrienes respectively. It is suggested (Srivastava and Mustafa; *Medical Hypotheses*, 1992, 39 342-348) that at least one of the mechanisms by which ginger shows its ameliorative effects could be related to inhibition of prostaglandin and leukotriene biosynthesis, i.e. it works as a dual inhibitor of eicosanoid biosynthesis.

Many chemical investigations have been carried out on the constituents of the essential oil of ginger. All together more than 200 different volatiles have been identified in the essential oil of ginger. The essential oil of ginger contains a mixture of various terpenes as well as some other non-terpenoid compounds.

The active compounds of ginger which may be employed in the present invention include, but are not limited to, 1,8-cineole, 10-dehydrogingerdione, 10-gingerol, 6-gingerdione, 6-gingerol, 6-shogaol, 8-β-17-epoxy-λ-trans-12-ene-15,16-diol, 8-gingerol, 8-shogaol, 9-oxo-nerolidol, acetaldehyde, acetic acid, alanine, α-linolenic-acid, α-linotenic acid, α-phellandrene, α-piene, α-terpinene, α-terpineol, α-zingiberene, ar-curcumene, arginine, ascorbic acid, asparagine, β-bisabolol, β-carotene, β-elemene, β-eudesmol, β-ionone, β-myrcene, β-phellandrene, β-pinene, β-selinene, β-sesquiphellandrene, β-sitosterol, β-thujone, bornyl-acetate, boron, caffeic acid, calcium, camphene, camphor, capric acid, caprylic acid, capsaicin, caryophyllene, chavicol, chlorogenic acid, chromium, citral, citronellal, citronellal, cobalt, copper, cumene, curcumin, cystine, delphinidin, δ-cadinene, elemol, ethyl acetate, ethyl-myristate, farnesal, farnesene, ferulic acid, furfural, γ-aminobutyric acid, γ-terpinene, geranial, geraniol, geranyl-acetate, gingerenone, glutamic acid, glycine, hexahydrocurcumin, histidine, isogingerenone-B, isoleucine, kaempferol, lecithin, limonene, linoleic acid, magnesium, manganese, methionine, mufa, myrecene, myricetin, myristic acid, neral, nerol, nerolidol, niacin, nickel, oleic acid, oxalic acid, p-coumaric acid, p-cymene, p-hydroxy-benzoic acid, palmitic acid, pantothenic acid, paradol, patchoulic alcohol, phenylalanine, quercetin, riboflavin, selenium, shikimic-acid, terpinen-4-ol, thiamin, tryptophan, vanillic acid, vanillin, zinc, and zingerone. Also, mixtures of two or more of these active compounds may be employed.

The first ingredient of the composition of the present invention, which may be obtained from ginger, can be incorporated in the anti-microbial composition of the present invention in many different forms including extracts such as ginger powder extracts, ginger fluid extracts, ginger powder including ginger root powder, and one or more active compounds of ginger, parts of, or whole ginger plants, tinctures thereof, and mixtures thereof. Preferably, the first ingredient of the anti-microbial composition of the present invention is selected from ginger extract, and ginger root powder.

Each gram of the anti-microbial composition of the present invention preferably contains about 30 mg to about 150 mg of ginger root powder. Most preferably, each gram of the anti-microbial composition contains about 50 mg to about 110 mg of ginger root powder. These ranges use, as a baseline, the use of Ginger Root Powder, ex. Stryka Botanics in the ingested formulation and Ginger Extract K (Aquaresin Ginger), ex. Kalsec, Inc. of Kalamazoo, Mich. in the spray formulation.

The amounts of various ingredients are given herein in terms of one form of the ingredient, i.e. ginger root powder. If that ingredient is present in another form, then the amount to be employed is that amount which will provide the same amount of the one or more active compounds as the amount of that ingredient given herein. For example, if a tincture of ginger is employed, the amount of the tincture employed will be the amount that provides the same amounts of one or more active compounds as would be provided by the amounts of ginger root powder specified above. This applies to all ingredients for which the amounts are given herein for one particular form of that ingredient.

The second ingredient of the anti-microbial composition of the present invention may be obtained from green tea. The second ingredient obtained from green tea may have an anti-oxidant effect.

Green tea is the dried leaves and leaf buds of the shrub *Camellia sinensis*. It is mainly produced in China and Japan. Dried tea leaves are composed mainly of phytochemicals known as polyphenols (about 36%), principally flavonols (including catechins), flavonoids, and flavondiols. The leaves also contain plant alkaloids (about 4%), including caffeine, theobromine and theophylline. Much of the research on green tea has been focused on its potential to prevent cancer. Research suggests that the polyphenols in green tea are responsible for a chemopreventive effect (E. Kaegi, *Canadian Medical Association Journal*, 1998, 158: 1033-35).

The pharmacological activities of green tea are mainly due to its active compounds. The active compounds of green tea useful in the present invention include, but are not limited to, flavonols, catechins, flavonoids, flavondiols, plant alkaloids, caffeine, theobromine, theophylline, phenolic acids, proteins, carbohydrates, and minerals.

The second ingredient which may be obtained from green tea, can be included in the anti-microbial composition in the form of green tea powder, green tea extracts such as green tea powder extracts, green tea fluid extracts, and one or more active compounds of green tea, part of, or whole green tea plants, green tea leaves, tinctures thereof, or mixtures thereof. Preferably, the second ingredient of the anti-microbial composition of the present invention is selected from green tea leaves, green tea powder and green tea extract. More preferably, the second ingredient of the anti-microbial composition of the present invention is green tea extract.

Each gram of the anti-microbial composition of the present invention preferably contains about 5 mg to about 20 mg of green tea extract. Most preferably, each gram of the anti-microbial composition contains about 7 mg to about 15 mg of green tea extract. These ranges use, as a baseline, the use of Green Tea, ex. Stryker Botanics in the ingested formulation and Green Tea Extract, ex. Phytoway, Inc., ChanSha, P.R. China, in the spray formulation.

Also preferably, the anti-microbial composition of the present invention includes, as an optional ingredient, one or more ingredients obtainable from turmeric, in a safe and effective amount to provide one or more of the beneficial effects described herein.

Turmeric (*Curcuma longa*), or Haldi in Hindi, is used very widely as medicine as well as a common ingredient in Indian cooking. The rhizome of turmeric is used in medicine and food as a fine powder.

Anti-inflammatory effects of curcumin isolated from *Curcuma longa* were reported in Srimal and Dhawan, Pharmacology of Diferuloyl Methane, a Non-steroidal Anti-inflammatory Agent, *J. Pharm. Pharmac.*, 25:447-452 (1973). Significant anti-inflammatory activity for curcumin, comparable with phenylbutazone and hydrocortisone, was observed by Arora et al. (*Indian Journal of Medical Research*, 1971, 59, 1289-1291). Curcumin, an alkaloid (diferuloyl methane) isolated from the alcoholic extract of turmeric, has been shown to be a potent anti-inflammatory agent. Further work on anti-inflammatory and anti-arthritic activity has also been carried out by Thatte et al. (*Indian Journal of Pharmacology*, 1986, 18 (1), 19-21). Turmeric has been found to have significant anti-inflammatory activity both in acute and chronic models.

The therapeutic dose of turmeric, for optimal activity if used alone, is reported to be in the range of about 5 to about 10 grams of dry powder daily (Patwardhan, U.S. Pat. No. 5,494,668). This dosage level, however, can produce a feeling of nausea.

Curcumin not only has anti-inflammatory properties but also has anti-oxidant, anti-tumor and other valuable properties. When used in low concentrations, curcumin can inhibit nitric oxide synthase (NOS) and, therefore, inhibit nitric oxide production. For example, Brouet et al. (*Biochem. Biophys. Res. Commun.*, Jan. 17, 1995; 206 (2); 533-40) have reported that NOS activity in soluble extracts of macrophages activated for 6-24 hours in the presence of curcumin (10 microM) was significantly lower that that of macrophages activated without curcumin. Northern-blot and immunoblotting analyses demonstrated that significantly reduced levels of the mRNA and 130-k Da protein of inducible NOS were expressed in macrophages activated with curcumin, compared to those without curcumin activation. Inhibition of NOS induction was maximal when curcumin was added together with lipopolysaccharide (LPS) and interferon-gamma (IFN-gamma) and decreased progressively as the interval between curcumin and LPS/IFN-gamma was increased to 18 hours.

The yellow pigment of the rhizome of turmeric is composed of three compounds known as curcuminoids. The three curcuminoids are curcumin (diferuloylmethane), desmethoxycurcumin (hydroxycinnamoyl feruloylmethane), and bis-desmethoxycurcumin (dihydroxydicinnamoyl methane) (see Drug Analysis by Chromatography and Microscopy, p. 169, Ann Arbor Science Inc., 1973). The essential oils of turmeric (*curcuma longa*) are primarily composed of the following compounds: d-camphor (about 1%), cyclo-isoprenemyrcene (about 85%), and p-tolylmethylcarbinol (about 5%), (see E. Gunther, *The Essential Oil*, pp. 123-4, Van Nostrand Co., 1955).

The optional ingredient of the composition of the present invention, obtained from turmeric, preferably includes curcuminoids, such as curcumin (diferuloylmethane), desmethoxycurcumin (hydroxycinnamoyl feruloylmethane), and bis-desmethoxycurcumin (dihydroxydicinnamoyl methane), and mixtures of two or more of these curcuminoids.

Methods for isolating curcuminoids from turmeric are known (see Janaki and Bose, An Improved Method for the Isolation of Curcumin From Turmeric, J. Indian Chem. Soc. 44:985 (1967)). Alternatively, curcuminoids for use in the present invention can be prepared by synthetic methods.

The optional ingredient, which can be obtained from of turmeric, can be incorporated into the composition of the present invention in a variety of different forms. Those different forms preferably include extracts of turmeric such as turmeric powder extracts, turmeric fluid extracts, one or more the curcuminoid compounds, and turmeric powder, parts of, or whole plants of turmeric, tinctures thereof, and mixtures thereof. More preferably, the optional ingredient obtainable from turmeric is a turmeric extract.

When the optional ingredient obtainable from turmeric is used, each gram of the anti-microbial composition of the present invention preferably contains about 5 mg to about 20 mg of turmeric powder extract. Most preferably, each gram of the anti-microbial compositions contains about 7 mg to about 15 mg of turmeric powder extract. These ranges are based on the use of Turmeric Extract 95%, ex. Pharmline, Inc. in the ingested formulation and Turmeric Root Extract (Oleoresin Turmeric), ex. Kalsec, Inc., Kalamazoo, Mich., in the spray formulation.

The ingredients of the anti-microbial composition of the present invention, which may be obtained from ginger and green tea, and, optionally, turmeric, may be used in the forms of turmeric powder, ginger powder and green tea powder, each of which may be ground from the rhizome of turmeric, ginger root and green tea leaves, respectively. For a particular active compound of ginger, green tea or turmeric, for which a synthetic route is known, the active compound may be synthesized. The plant extracts, if desired, may be prepared as described below. Alternatively, turmeric powder, ginger powder, green tea powder and/or one or more of the active compounds contained therein may be purchased from commercial sources such as the Delavau Co. of Philadelphia, Pa.

The plant extracts, e.g., turmeric extract, ginger extract and green tea extract, that may be used in the compositions of the invention, may be produced using common extraction procedures. Alternatively, the extracts may be purchased from commercial sources such as the Delavau Co. of Philadelphia, Pa.

One suitable extraction procedure comprises, generally, the steps of:

1) cleaning the plant from which the pharmacologically or biologically active plant extract is to be obtained to remove any foreign matter thereon;
2) particulating the plant to obtain a particulate mass having particle size ranging from 0.001 to about 10 $mm^3$; and
3) subjecting the particulate mass to at least one polar and at least one non-polar solvent to obtain separate fractions of plant extract soluble in the respective solvents, and mixing the fractions so obtained to obtain the beneficiated plant extract in accordance with this invention.

For instance, in the case of turmeric, the process comprises the steps of:

1) cleaning the roots of turmeric to remove any foreign matter thereon;
2) particulating the roots to obtain a particulate mass having particle size ranging from 0.001 to about 10 $mm^3$;
3) subjecting the particulate mass to distillation to obtain a volatile fraction, if any, from the particulate mass;
4) cooking the distilled particulate mass in a polar solvent, such as water to solubilize material in the distillation-treated particulate mass to obtain first solution and a first residue;
5) filtering the first solution from the first residue;
6) evaporating the filtrate obtained from the first solution to remove the solvent and obtain a solute designated as fraction A obtained from the particulate mass;
7) subjecting the first residue to treatment with a second polar solvent such as 75% to 95% ethanol for twelve to thirty-six hours to obtain a second solution and a second residue;
8) filtering the second solution from the second residue to obtain a second filtrate;
9) evaporating the second filtrate to remove its solvent and obtain a solute designated as fraction B obtained from the particulate mass;
10) subjecting the second residue to less polar or non-polar solvents, such as petroleum ether, for twelve to thirty-six hours to obtain a third solution and a third residue, and filtering the third solution from the third residue to obtain a third filtrate;
11) evaporating the third filtrate to remove its solvent and obtain a solute designated as fraction C obtained from the particulate mass; and
12) homogeneously mixing the volatile fraction, with fractions A, B and C from the particulate mass to obtain a beneficiated plant extract.

The process is suitable for the preparation of pharmacologically or biologically active plant extracts in a convenient, administrable dosage form from any of the plants mentioned above.

Solvents useful for extracting turmeric include water, ethanol, propanol, paraffin, hexane, petroleum ether, toluene, acetone, methyl ethyl ketone, and other common organic solvents. Water, ethanol and petroleum ether are the preferred solvents for extracting turmeric. Solvents useful for extracting ginger include water, ethanol, propanol, paraffin, petroleum ether, hexane, toluene, acetone, methyl ethyl ketone, and other common organic solvents. Ethanol, water and acetone are the preferred solvents for extracting ginger.

The anti-microbial composition of the present invention may be used to treat microbial infection, since the composition of the present invention has significant anti-microbial properties as demonstrated by the examples of this application. The anti-microbial composition of the present invention may also be used as a therapeutic composition to treat one or more symptoms of a microbial infection, including sore throat, congestion, laryngitis, mucositis, and/or mucous membrane inflammation by administration to a patient suffering from one or more of these symptoms or ailments.

Viruses that may be inhibited by the anti-microbial composition of the present invention includes, among other viruses, rhinoviruses, respiratory syncytial virus (RSV), Herpes viruses, influenza viruses, HIV-viruses and the West Nile virus.

In a preferred embodiment, the viruses that may be inhibited by the anti-microbial composition include at least human rhinovirus 16, Herpes I Virus (HSV-1), Influenza A/Moscow/10/99, and B/Guangdong/120/00.

The anti-microbial composition of the present invention may also be used to treat bacterial infections, such as streptococcal infections, and fungal infections, for example by yeasts such as *Candida*.

Preferably, the anti-microbial composition of the present invention may be formulated in any acceptable dosage form including, but not limited to, capsules, tablets, lozenges, troches, hard candies, powders, sprays, gels, elixirs, syrups, and suspensions or solutions. The anti-microbial composition of the present invention may also be administered in the form of a nutritional supplement, in which case the composition of the invention may be the nutritional supplement or may form a part of a nutritional supplement containing additional ingredients.

The anti-microbial composition of the present invention may also be formulated with an acceptable carrier. The acceptable carrier may include, but is not limited to: (a) carbohydrates including sweeteners, more preferably, fructose, sucrose, sugar, dextrose, starch, lactose, maltose, maltodextrins, corn syrup solids, honey solids, commercial tablet nutritional supplements including Emdex™, Mor-Rex™, Royal-T™, Di-Pac™, Sugar-Tab™, Sweet-Rex™, and New-Tab™; (b) sugar alcohols including mannitol, sorbitol and xylitol; and (c) various relatively insoluble excipients including dicalcium phosphate, calcium sulfate, calcium carbonate, microcrystalline cellulose and other tableting ingredients.

Lozenges, tablets, and troches in this invention may differ in shape, size and manufacturing technique. In the case of tablets, for oral use, the acceptable carrier may further include lactose and corn starch. Lubricating agents may also be added to the tablets, including, for example, magnesium stearate, sodium lauryl sulfate and talc. Tablets may also contain excipients such as sodium citrate, calcium carbonate and calcium phosphate. Disintegrants such as starch, alginic acid and complex silicates, may also be employed. Tablets may also include binding agents such as polyvinylpyrrolidone, gelatin, PEG-8000 and gum acacia.

In the case of lozenges for oral use, the common acceptable carrier may further include a binder such as PEG-8000. Preferably lozenges weigh about 0.1 to about 15 grams to provide a suitable dissolution rate when taken orally. More preferably, lozenges weigh about 1 to about 6 grams.

To make compressible lozenges, the active ingredients are added to PEG-8000 processed fructose; or the active ingredients of the anti-microbial composition are added to crystalline fructose and commercially available, sweet, direct compression products such as Mendell's Sugartab™, Sweetrex™, or Emdex™. Sweeteners such as saccharin may be added, if desired, flavors as desired, glidants, such as silica gel, as needed, and lubricants, such as magnesium stearate, as needed. The mixture should be kept dry and tableted soon after mixing. The ingredients are mixed and directly compressed into lozenges using conventional pharmaceutical mixing and tableting equipment. The compressive force is preferably sufficient to produce maximum hardness throughout the lozenges, to preserve a suitable dissolution rate, and to maximize the efficacy of the lozenges. Dissolution of the lozenges, when taken orally, should occur over a sustained period of time, that being about 5 to 60 minutes, and preferably about 20 to 30 minutes. The anti-microbial composition is preferably stored in an airtight container and in a cool dark place.

Tablets and troches can be manufactured using procedures similar to that described above with minor changes in the optional ingredients. Such changes are within the skill of the ordinary skilled artisan.

Alternatively, the anti-microbial composition of the present invention may be formulated in liquid form, such as syrups, mouthwashes or sprays, with a solvent or dispersant such as water, or other liquids and optionally in a pharmaceutically acceptable carrier, for repeated delivery of the anti-microbial composition to oral and oropharyngeal mucous membranes over a sustained period of time. Preferably, the treatment time is about 5 to 60 minutes, and more preferably about 20 to 30 minutes, so as to permit a prolonged contact of the anti-microbial composition with mouth and throat tissues. Alternatively, such formulations can be in a concentrated form suitable for dilution with water or other materials prior to use.

The anti-microbial composition may also be formulated in chewable forms, such as soft candy, gum drops, liquid filled candies, and chewing gum bases, or in the form of dental products, such as toothpastes and mouthwashes. In use, the chewable composition is preferably retained in the mouth over a sustained period of time of preferably about 5 to 60 minutes, and more preferably about 20 to 30 minutes. Dental products may be used in the ordinary manner of using such products.

The anti-microbial composition of the invention may be formulated in capsule form, with or without diluents. For capsules, useful diluents include lactose and dried corn starch. When suspensions are employed, emulsifying and/or suspending agents may be employed in the suspensions. In addition, solid compositions including one or more of the ingredients of the lozenges described above may be employed in soft and hard gelatin capsules.

The anti-microbial composition of the present invention may also be formulated into a nasal aerosol or inhalant composition. Such a composition may be prepared using well-known techniques. For these types of formulations, suitable carriers may include the following ingredients: saline with one or more preservatives, absorption promoters to enhance bioavailability, fluorocarbons, and/or conventional solubilizing or dispersion agents.

Other materials, which may optionally be included in the anti-microbial composition of the present invention, include resveratrol (trihydroxystilbene), inositol, other B-complex vitamins, and additional anti-inflammatories. Also, ingredients such as sweeteners, flavorants, coloring agents, dyes, preservatives, emulsifying agents, suspending agents, melting agents, excipients, demulcents and solvents or diluents such as water, ethanol, propylene glycol, glycerin and various combinations thereof, may be included in the anti-microbial composition of the present invention.

The optional sweeteners which may be used in the anti-microbial composition of the present invention include, but are not limited to, saccharin, aspartame, cyclamates, acesulfame K, neohesperidin dihydrochalcone, other super sweeteners, and mixtures thereof, which may be added to the carrier in amounts sufficiently low so as not to chemically interact with the main ingredients of the anti-microbial composition.

The optional flavorants which may be used in the anti-microbial composition of the present invention include, but are not limited to, peppermint, peppermint-menthol, eucalyptol, wintergreen, licorice, clove, cinnamon, spearmint, cherry, lemon, orange, lime, menthol and various combinations thereof.

Preferably, the main ingredients described above, that may be derived from ginger and green tea, make up from about 0.5 to about 90% by weight of the total composition. More preferably, the main ingredients will make up about 10 to about 70% by weight of the total composition. Most preferably, the main ingredients make up about 20 to about 40% by weight of the total composition.

The non-carrier ingredients of the anti-microbial composition, including the ingredients obtainable from turmeric, ginger, and green tea as discussed above, can be increased or decreased proportionally in the anti-microbial composition of the present invention depending on the amount of carrier used in the anti-microbial composition, without substantially affecting the effectiveness of the anti-microbial composition for its intended use.

In another aspect, the present invention relates to a method of reducing, treating or preventing of at least one symptom or adverse effect of microbial infection by administering, to a patient infected with a microbe, an anti-microbial composition of the present invention, including ingredients that can be obtained from ginger and green tea.

In the method, the patient may be a human, an in vitro cell, or an animal. Preferably, the patient is a mammal; more preferably, a human. In the method, the virus that may be inhibited by administration of the anti-microbial composition of the present invention includes, among other viruses, rhinoviruses, respiratory syncytial virus (RSV), Herpes viruses, influenza viruses, HIV-viruses and the West Nile virus. In a preferred embodiment, the viruses that may be inhibited by administration of the anti-microbial composition include at least human rhinovirus 16, Herpes I Virus (HSV-1), Influenza A/Moscow/10/99, and B/Guangdong/120/00.

The anti-microbial composition of the present invention may also be used to treat bacterial infections, such as streptococcal infections, and fungal infections, for example by yeasts such as *Candida*.

The symptoms, caused by a microbial infection, that may be treated, reduced, or at least partially prevented by this method of the present invention, may include one or more of headache, joint pain, fever, cough, sneezing, muscle ache, running nose, dry mouth, dizziness, and other symptoms related to microbial infection.

The effective amount of the anti-microbial composition will vary depending on such factors as the patient being treated, the particular mode of administration, the activity of the particular active ingredients employed, the age, bodyweight, general health, sex and diet of the patient, time of administration, rate of excretion, the particular combination of ingredients employed, the total content of the main ingredient of the composition, and the severity of the illness or symptom. It is within the skill of the person of ordinary skill in the art to account for these factors.

The anti-microbial composition may be administered about 1 to about 15 times per day, as needed, more preferably, about 2 to about 12 times per day, as needed, or most preferably, about 6 to about 10 times per day, as needed. The anti-microbial composition of the present invention may be administered in any acceptable dosage form including, but not limited to, tablets, capsules, lozenges, troches, hard candies, powders, oral sprays, nasal sprays, gels, elixirs, syrups, chewable compositions, dental products, suspensions, and solutions.

Each dosage of the anti-microbial composition contains a safe and effective amount of the anti-microbial composition of the present invention. An effective amount for each therapeutic administration contains a total of about 0.1 gram to about 1 gram of the ingredients, which may be obtained from ginger and green tea. More preferably, an effective amount of the anti-microbial composition for each therapeutic administration contains a total of about 0.2 gram to about 0.5 gram of the ingredients which may be obtained from ginger and green tea. The amounts of the various ingredients of the composition administered in accordance with the method of the present invention are the same as given above for the composition of the present invention.

Preferably, during each oral administration of the anti-microbial composition, the composition is held in the mouth for at least about 5 to about 60 minutes to enable the main ingredients of the anti-microbial composition to contact the mouth tissue or throat before it completely dissolves. More preferably, the anti-microbial composition is held in the mouth for at least about 15 to about 30 minutes.

The following preferred ranges define compositions according to the invention that are suited for administration in a spray formulation according to the methods of the invention.

Each gram of the antimicrobial composition administered in a spray according to the methods of the present invention preferably contains about 1 mg to about 10 mg of aquaresin ginger. Most preferably, each gram of the antimicrobial composition contains about 3 mg to about 7 mg of aquaresin ginger.

Each gram of the anti-microbial composition administered in a spray according to the methods of the present invention preferably contains about 1 mg to about 20 mg of green tea leaf extract. Most preferably, each gram of the anti-microbial composition contains about 7 mg to about 15 mg of green tea leaf extract.

When an optional ingredient from turmeric is used, each gram of the anti-microbial composition administered in a spray according to the methods of the present invention preferably contains about 1 mg to about 12 mg of soluble oleoresin turmeric. Most preferably, each gram of the anti-microbial composition contains about 4 mg to about 9 mg of soluble oleoresin turmeric.

As discussed above, the composition of the present invention may be administered in any orally acceptable dosage form including, but not limited to tablets, capsules, lozenges, troches, hard candies, powders, oral sprays, nasal sprays, gels, elixirs, syrups, chewable compositions, dental products, suspensions, and solutions.

The invention will be further illustrated by the examples given below which are not to be construed as limiting the invention in any way. The scope of the invention is to be determined by the claims appended hereto.

EXAMPLE 1

An Anti-microbial Composition of the Present Invention

An anti-microbial composition of the present invention formulated in the form of lozenges was prepared using the procedure described above. The ingredients of the lozenge are listed below:

| | |
|---|---|
| Sugar | 1 g |
| Slippery elm bark | 118 mg |
| Turmeric extract (5% curcumin) | 18 mg |
| Ginger root | 140 mg |
| Horseradish root | 70 mg |
| Green tea leaf extract (30% catechin and polyphenols) | 14 mg |

EXAMPLE 2

Treatment of Sore Throat

Each of seven patients, suffering from sore throats, ingested one lozenge formulated according to Example 1 every two hours by holding the lozenge in his or her mouth for about 15-30 minutes until the lozenge completely dissolved. No patient took more than 10 lozenges in any given day.

The patients that were treated reported complete relief from the symptoms of their sore throats after ingesting from 2 to 20 lozenges. It was also found that each lozenge can provide relief from a sore throat for up to 6 hours.

EXAMPLE 3

In Vitro Testing of Virucidal Activity of the Anti-microbial Composition

The in vitro testing protocol for virucidal activity employed in this example uses human rhinovirus 16 (hereafter "HRV-16") as the target virus, and the MRC-5 cell line related to human tissues described by Jacobs, et al, *Characteristics of Human diploid MRC-5*, Nature (London), 227, p 168-170 (1970) as the host cell for the HRV-16 viruses. Residual virus infectivity following incubation of the test substances with the virus was titrated on the MRC-5 cell line for rhinovirus growth by visually scoring the cytopathic effect (CPE) induced by virus replication through microscopic observation. More specifically, CPE was scored by observing ballooning/rounded cells in the MRC-5 culture.

To determine the virucidal activity, the anti-microbial composition of Example 1 (hereafter "Substance 1"), was employed at an initial dilution of 1/20 and then further diluted by serial dilutions in saline. The diluted compositions were incubated with HRV-16 for a set time period and then the reaction was terminated by adjustment to a neutral pH with cell infection media. The resultant solution was then titrated out on MRC-5 cells at a dilution of 1/10 across a testing plate to carry out the infection of the cells. Each plate housed a virus control, which contained only HRV-16 infected MRC-5 cells, and a cell control, which contained only uninfected MRC-cells.

The plates were further incubated for 4 days after the infection. Residual viral infectivity was measured using the assay discussed above. From the results shown in Tables 1-4, all of the controls on the plate worked well.

From the assay, it was concluded that Substance 1, at a 1/20 dilution, was effective in producing an HRV-16 viral log reduction of 1.50 (−log 10 TCID50) at the 1-minute incubation period. A 1/40 dilution of Substance 1 produced a log reduction of 1.00 (−log 10 TCID50) also at the 1-minute incubation period. After the 2-minute and 5-minute incubation periods, 1/2 log reductions in HRV-16 titre were achieved. Therefore, these results tend to indicate that a 1-minute contact time between Substance 1 and HRV-16 would produce the most effective viral titre reduction.

Table 1 shows the residual virus titres and log reductions of infectious Rhinovirus 16 on MRC-5 cells at one termination time point, of Substance 1 at different dilutions.

TABLE 1

| Dilutions | pH value of Substance 1 in Isotonic solution | pH value of terminated solution | Virus Control (TCID50) | 1 Minute Incubation Residual Virus titre (TCID50) | Log Reductions (TCID50) |
| --- | --- | --- | --- | --- | --- |
| 1/20 | 5.03 | 7.73 | 3.80 | 2.30 | 1.50 |
| 1/40 | 5.13 | 7.77 | 3.80 | 3.30 | 0.50 |
| 1/80 | 4.98 | 7.83 | 3.80 | 3.80 | 0.00 |
| 1/160 | 4.98 | 7.73 | 3.80 | 3.80 | 0.00 |

Tables 2-4 show the results of a second trial on the residual virus titres and the log reductions of infectious HRV-16 on MRC-5 cells at three different termination time points, of Substance 1 at different dilutions.

TABLE 2

| Dilutions of Substance 1 | HRV-16 Control Titre (TCID50) | 1 Minute Incubation Residual HRV-16 titre (TCID50) | HRV-16 log Reductions (TCID50) |
| --- | --- | --- | --- |
| 1/20 | 3.30 | 1.80 | 1.50 |
| 1/40 | 3.30 | 2.30 | 1.00 |
| 1/80 | 3.30 | 2.80 | 0.50 |
| 1/160 | 3.30 | 2.80 | 0.50 |
| 1/320 | 3.30 | 2.80 | 0.50 |

TABLE 3

| Dilutions of Substance 1 | HRV-16 Control Titre (TCID50) | 2 Minute Incubation Residual HRV-16 titre (TCID50) | HRV-16 log Reductions (TCID50) |
| --- | --- | --- | --- |
| 1/20 | 3.30 | 2.80 | 0.50 |
| 1/40 | 3.30 | 2.80 | 0.50 |
| 1/80 | 3.30 | 2.80 | 0.50 |
| 1/160 | 3.30 | 2.80 | 0.50 |
| 1/320 | 3.30 | 2.80 | 0.50 |

TABLE 4

| Dilutions of Substance 1 | HRV-16 Control Titre (TCID50) | 5 Minute Incubation Residual HRV-16 titre (TCID50) | HRV-16 log Reductions (TCID50) |
| --- | --- | --- | --- |
| 1/20 | 3.30 | 2.80 | 0.50 |
| 1/40 | 3.30 | 2.80 | 0.50 |
| 1/80 | 3.30 | 2.80 | 0.50 |
| 1/160 | 3.30 | 2.80 | 0.50 |
| 1/320 | 3.30 | 2.80 | 0.50 |

Similar virucidal tests have been carried out for Substance 1 using other viruses, including Herpes I Virus (HSV-1) using Vero cells as the host cell, Influenza A/Moscow/10/99, and B/Guangdong/120/00 using MDCK cells as the host cell. The results on these virucidal tests are summarized below in Tables 5-13.

Tables 5-7 show the residual virus titres and log reductions of infectious HSV-1 on Vero cells at three different termination time points, of Substance 1 at different dilutions.

TABLE 5

| Dilutions of Substance 1 | HSV-1 Control Titre (−log 10 TCID50) | 1 Minute Incubation Residual HSV-1 titre (−log 10 TCID50) | HSV-1 log reductions (−log 10 TCID50) |
| --- | --- | --- | --- |
| 1/40 | 3.80 | 0.00 | 3.80 |
| 1/80 | 3.80 | 0.00 | 3.80 |
| 1/160 | 3.80 | 2.80 | 1.00 |
| 1/320 | 3.80 | 2.80 | 1.00 |
| 1/640 | 3.80 | 2.80 | 1.00 |

TABLE 6

| | 2 Minute Incubation | | |
|---|---|---|---|
| Dilutions of Substance 1 | HSV-1 Control Titre (−log 10 TCID50) | Residual HSV-1 titre (−log 10 TCID50) | HSV-1 log reductions (−log 10 TCID50) |
| 1/40 | 3.80 | 0.00 | 3.80 |
| 1/80 | 3.80 | 0.00 | 3.80 |
| 1/160 | 3.80 | 1.80 | 2.00 |
| 1/320 | 3.80 | 2.80 | 1.00 |
| 1/640 | 3.80 | 2.80 | 1.00 |

TABLE 7

| | 5 Minute Incubation | | |
|---|---|---|---|
| Dilutions of Substance 1 | HSV-1 Control Titre (−log 10 TCID50) | Residual HSV-1 titre (−log 10 TCID50) | HSV-1 log reductions (−log 10 TCID50) |
| 1/40 | 3.80 | 0.00 | 3.80 |
| 1/80 | 3.80 | 0.00 | 3.80 |
| 1/160 | 3.80 | 1.80 | 2.00 |
| 1/320 | 3.80 | 2.80 | 1.00 |
| 1/640 | 3.80 | 2.80 | 1.00 |

Tables 8-10 show the residual virus titres and log reductions of influenza A/Moscow/10/99 at three different termination time points, of Substance 1 at different dilutions.

TABLE 8

| | 1 Minute Incubation | | |
|---|---|---|---|
| Dilutions of Substance 1 | A/Moscow Virus Titre (−log 10 TCID50) | Residual A/Moscow titre (−log 10 TCID50) | A/Moscow log reductions (−log 10 TCID50) |
| 1/10 | 2.80 | 0.00 | 2.80 |
| 1/20 | 2.80 | 0.00 | 2.80 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 9

| | 2 Minute Incubation | | |
|---|---|---|---|
| Dilutions of Substance 1 | A/Moscow Virus Titre (−log 10 TCID50) | Residual A/Moscow titre (−log 10 TCID50) | A/Moscow log reductions (−log 10 TCID50) |
| 1/10 | 2.80 | 0.00 | 2.80 |
| 1/20 | 2.80 | 0.00 | 2.80 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 10

| | 5 Minute Incubation | | |
|---|---|---|---|
| Dilutions of Substance 1 | A/Moscow Virus Titre (−log 10 TCID50) | Residual A/Moscow titre (−log 10 TCID50) | A/Moscow log reductions (−log 10 TCID50) |
| 1/10 | 2.80 | 0.00 | 2.80 |
| 1/20 | 2.80 | 0.00 | 2.80 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 0.00 | 2.80 |

Tables 11-13 show the residual virus titres and log reductions of Influenza B/Guangdong/120/00 at three different termination time points, of Substance 1 at different dilutions.

TABLE 11

| | 1 Minute Incubation | | |
|---|---|---|---|
| Dilutions of Substance 1 | B/Guangdong Virus Titre (−log 10 TCID50) | Residual B/Guangdong titre (−log 10 TCID50) | B/Guangdong log reductions (−log 10 TCID50) |
| 1/10 | 1.80 | 0.00 | 1.80 |
| 1/20 | 1.80 | 0.00 | 1.80 |
| 1/40 | 1.80 | 1.80 | 0.00 |
| 1/80 | 1.80 | 1.80 | 0.00 |
| 1/160 | 2.30 | 1.80 | 0.50 |
| 1/320 | 2.30 | 1.80 | 0.50 |
| 1/640 | 1.80 | 2.30 | −0.50 |
| Citrate Buffer | 1.80 | 0.00 | 1.80 |

TABLE 12

| | 2 Minute Incubation | | |
|---|---|---|---|
| Dilutions of Substance 1 | B/Guangdong Virus Titre (−log 10 TCID50) | Residual B/Guangdong titre (−log 10 TCID50) | B/Guangdong log reductions (−log 10 TCID50) |
| 1/10 | 1.80 | 0.00 | 1.80 |
| 1/20 | 1.80 | 0.00 | 1.80 |
| 1/40 | 1.80 | 1.80 | 0.00 |
| 1/80 | 1.80 | 1.80 | 0.00 |
| 1/160 | 2.30 | 1.80 | 0.50 |
| 1/320 | 2.30 | 1.80 | 0.50 |
| 1/640 | 1.80 | 2.80 | −1.00 |
| Citrate Buffer | 1.80 | 0.00 | 1.80 |

TABLE 13

| | 5 Minute Incubation | | |
|---|---|---|---|
| Dilutions of Substance 1 | B/Guangdong Virus Titre (−log 10 TCID50) | Residual B/Guangdong titre (−log 10 TCID50) | B/Guangdong log reductions (−log 10 TCID50) |
| 1/10 | 1.80 | 0.00 | 1.80 |
| 1/20 | 1.80 | 0.00 | 1.80 |
| 1/40 | 1.80 | 1.80 | 0.00 |
| 1/80 | 1.80 | 1.80 | 0.00 |
| 1/160 | 2.30 | 1.80 | 0.50 |
| 1/320 | 2.30 | 1.80 | 0.50 |

TABLE 13-continued

|  | 5 Minute Incubation | | |
| --- | --- | --- | --- |
| Dilutions of Substance 1 | B/Guangdong Virus Titre (−log 10 TCID50) | Residual B/Guangdong titre (−log 10 TCID50) | B/Guangdong log reductions (−log 10 TCID50) |
| 1/640 | 1.80 | 2.80 | −1.00 |
| Citrate Buffer | 1.80 | 0.00 | 1.80 |

In Tables 1-13, TCID50=−log 10 TCID50.

As one can see from above results, Substance 1 is effective in inhibiting or exterminating influenza viruses and human rhinoviruses. As a result, Substance 1 should be effective in treating influenza and common colds.

EXAMPLE 4

In Vitro Testing of Virustatic Activity of the Anti-microbial Composition

The in vitro testing protocol for virucidal activity employed in this example used human rhinovirus 16 (HRV-16) as the target virus, and the rhinovirus sensitive Hela cell line related to human tissues described by Conant et al, *Basis for a numbering system. I. Hela cells for propagation and serologic procedure*, J. Immunol., 100, p 107-113 (1968) as the host cell for the HRV-16 virus.

The anti-microbial composition of Example 1, Substance 1, was dissolved in infection media to the following dilutions: 1/20, 1/40, 1/80, 1/160 and 1/320. These dilutions were incubated on plates of MRC-5 cells for 30 minutes at 37° C. (5% $CO_2$). After the incubation period, each Substance 1 dilution with MRC-5 cells in a well of the plates was subjected to HRV-16 at a known titre of 2.30 (−log 10 TCID50). Each plate housed a virus control (the Hela cells infected with HRV-16 viruses and without Substance 1), a cell control (Hela cells only) and the test compound controls at the different dilutions (Hela cells with the test substance only). All the other samples on the plate contained the Hela cells infected with HRV-16 viruses and Substance 1 at different dilutions. The plates were further incubated for 4 days after infection.

Residual virus infectivity following incubation of Substance 1 with the virus was titrated on the Hela cell line for rhinovirus growth by measuring the cytopathic effect (CPE) induced by the virus using the following procedure.

The remaining viable Hela cells after incubation with Substance 1 were stained with crystal violet solution. Excess crystal violet was removed by washing and the crystal violet stained cells were solubilized using a mixture of methanol and acetic acid. The absorbance of the solution was then measured at 540 nm in an ELISA plate reader. The level of virus induced CPE was inversely proportional to the absorbance.

The results generated from the crystal violet assay enabled the toxic concentration and the effective concentration of Substance 1 to be determined by fitting an equation, y=mx+c, wherein x corresponds to the dilution of Substance 1 and y corresponds to percentage of toxicity of Substance 1 to the cells. From this equation, the TC50 (concentration at which Substance 1 indicates 50% toxicity to the cells) is at a 1/571 dilution of Substance 1.

This result correlates well with the percentage of cell survivors at various dilution of Substance 1, which was also measured using the crystal violet assay, as shown in Table 14 below.

TABLE 14

| Dilution of Substance 1 without Virus | % Cell Survivors |
| --- | --- |
| 1/320 | 89.7 |
| 1/160 | 94.6 |
| 1/80 | 97.6 |
| 1/40 | 109.3 |
| 1/20 | 168.2 |

Using the same equation, wherein x still corresponds to the dilution of Substance 1 and y corresponds to the percent efficacy of Substance 1 in the presence of the virus, the EC50 (concentration at which the test substance indicates 50% efficacy in the presence of virus) was determined to be at a 1/51 dilution of Substance 1. This result correlates well with the percentage of viable cells at various dilutions of Substance 1 measured using the crystal violet assay, as shown in Table 15 below.

TABLE 15

| Substance 1 dilution and Virus | % Viable Cells |
| --- | --- |
| 1/320 + HRV-16 | 79.3 |
| 1/160 + HRV-16 | 62.3 |
| 1/80 + HRV-16 | 39.0 |
| 1/40 + HRV-16 | 15.9 |
| 1/20 + HRV-16 | −220.0 |

In Tables 14 and 15, % Cell Survivors=(Compound only/Cell only)×100; and % Viable Cells=(Cell only−Compound+Virus)/(Cell only−Virus only)×100.

"Compound only" denotes the measurement results for the wells containing only Hela cells and Substance 1 at a predetermined dilution.

"Cell only" denotes the measurement results for the wells containing only uninfected Hela cells.

"Compound+Virus" denotes the measurement results for the wells containing both the Hela cells infected with HRV-16 viruses and Substance 1 at a predetermined dilution.

"Virus Only" denotes the measurement results for the wells containing the Hela cells infected with HRV-16 only.

EXAMPLE 5

An Anti-microbial Lozenge of the Present Invention

An anti-microbial lozenge was made according to the formulation set forth below.

| 1) Dextrose | 865.0 mg |
| --- | --- |
| 2) Slippery Elm Bark | 150.0 mg |
| 3) Stearic Acid | 75.0 mg |
| 4) Ginger Root | 105.0 mg (Children) or 140.0 mg (Adult) |
| 5) Horseradish Root | 70.0 mg |
| 6) Honey Natural Flavor | 40.0 mg |
| 7) Turmeric Extract (5% Curcumin) | 15.0 mg |
| 8) Green Tea Leaf Extract (36% C&P) | 14.0 mg |
| 9) Silicon Dioxide | 14.0 mg |

-continued

| | | |
|---|---|---|
| 10) Magnesium Stearate | | 12.0 mg |
| 11) Sucralose/Splenda | | 4.0 mg |
| Tablet Weight: | | 1364.0 mg |

Note:
C&P as used herein means "catechols and phenols."

EXAMPLE 6

An Anti-microbial Spray of the Present Invention

An anti-microbial spray was made according to the formulation set forth below.

| (1) | Slippery Elm Bark Extract | 18.52 mg |
|---|---|---|
| (2) | Oleoresin Turmeric, Soluble (~8.5% Curcumin) | 8.82 mg |
| (3) | Aquaresin Ginger | 7.0 mg |
| (4) | Horseradish Flavor WONF | 0.62 mg |
| (5) | Green Tea Leaf PE 50% Colorimetric | 14.0 mg |
| (6) | Honey Natural Flavor | 40.0 mg |
| (7) | Ethanol (95%) @ 5% | 68.2 mg |
| (8) | Glycerine | 603.42 mg |
| (9) | Distilled Water | 603.42 mg |
| | Total Weight: | 1364.0 mg |

EXAMPLE 7

In Vitro Testing of Anti-microbial Lozenge

The anti-microbial lozenge of Example 5 was tested for virucidal and virustatic activity against infection of MDCK cells with influenza viruses of the strains A/NewCaledonia/20/99 ($H_1N_1$), A/Panama/2007/99 ($H_3N_2$), and B/Guangdong/120/00.

In determining virucidal the lozenge was tested at dilutions of 1/10, 1/20, 1/40, 1/80, 1/160, 1/320, and 1/640. The lozenge was diluted with saline isotonic solution (Normasol). Each dilution was tested at termination points of 1, 2, and 5 minutes after the lozenge came in contact with each virus. The reaction was terminated with 1.8 ml of 0% FBS cell media.

The log reductions in this example are reported as –log 10 TCID50 and were calculated using the Karber equation.

TABLE 16

The residual virus titres and log reductions of infectious A/New Caledonia/20/99 (H1N1) virus after the 1-minute termination time point at different dilutions.

| | 1 Minute Incubation | | |
|---|---|---|---|
| Dilution | A/New Caledonia Virus Titre (–log 10 TCID50) | Residual Influenza titre (–log 10 TCID50) | Virus log reductions (–log 10 TCID50) |
| 1/10 | 2.80 | 0.00 | 2.80 |
| 1/20 | 2.80 | 2.30 | 0.50 |
| 1/40 | 2.80 | 1.80 | 1.00 |
| 1/80 | 2.80 | 2.30 | 0.50 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 17

The residual virus titres and log reductions of infectious A/New Caledonia/20/99 (H1N1) virus after the 2-minute termination time point at different dilutions.

| | 2 Minute Incubation | | |
|---|---|---|---|
| Dilution | A/New Caledonia Virus Titre (–log 10 TCID50) | Residual Influenza titre (–log 10 TCID50) | Virus log reductions (–log 10 TCID50) |
| 1/10 | 2.80 | 0.00 | 2.80 |
| 1/20 | 2.80 | 1.80 | 1.00 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 18

The residual virus titres and log reductions of infectious A/New Caledonia/20/99 (H1N1) virus after the 5-minute termination time point at different dilutions.

| | 5 Minute Incubation | | |
|---|---|---|---|
| Dilution | A/New Caledonia Virus Titre (–log 10 TCID50) | Residual Influenza titre (–log 10 TCID50) | Virus log reductions (–log 10 TCID50) |
| 1/10 | 2.80 | 0.00 | 2.80 |
| 1/20 | 2.80 | 1.80 | 1.00 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 19

The residual virus titres and log reductions of infectious A/Panama/2007/99 (H3N2) virus after the 1-minute termination time point at different dilutions.

| | 1 Minute Incubation | | |
|---|---|---|---|
| Dilution | A/Panama Virus Titre (-log 10 TCID50) | Residual Influenza titre (–log 10 TCID50) | Virus log reductions (–log 10 TCID50) |
| 1/10 | 4.80 | 3.80 | 1.00 |
| 1/20 | 4.80 | 3.80 | 1.00 |
| 1/40 | 4.80 | 4.80 | 0.00 |
| 1/80 | 4.80 | 4.30 | 0.50 |
| 1/160 | 4.80 | 4.80 | 0.00 |
| 1/320 | 4.80 | 4.80 | 0.00 |
| 1/640 | 4.80 | 4.80 | 0.00 |
| Citrate Buffer | 4.80 | 0.00 | 4.80 |

TABLE 20

The residual virus titres and log reductions of infectious A/Panama/2007/99 (H3N2) virus after the 2-minute termination time point at different dilutions.

| | | 2 Minute Incubation | |
|---|---|---|---|
| Dilution | A/Panama Virus Titre (-log 10 TCID50) | Residual Influenza tire (-log 10 TCID50) | Virus log reductions (-log 10 TCID50) |
| 1/10 | 4.80 | 3.80 | 1.00 |
| 1/20 | 4.80 | 4.30 | 0.50 |
| 1/40 | 4.80 | 4.80 | 0.00 |
| 1/80 | 4.80 | 4.30 | 0.50 |
| 1/160 | 4.80 | 4.80 | 0.00 |
| 1/320 | 4.80 | 4.80 | 0.00 |
| 1/640 | 4.80 | 4.80 | 0.00 |
| Citrate Buffer | 4.80 | 2.30 | 2.50 |

TABLE 21

The residual virus titres and log reductions of infectious A/Panama/2007/99 (H3N2) virus after the 5-minute termination time point at different dilutions.

| | | 5 Minute Incubation | |
|---|---|---|---|
| Dilution | A/Panama Virus Titre (-log 10 TCID50) | Residual Influenza titre (-log 10 TCID50) | Virus log reductions (-log 10 TCID50) |
| 1/10 | 4.80 | 3.80 | 1.00 |
| 1/20 | 4.80 | 4.30 | 0.50 |
| 1/40 | 4.80 | 4.80 | 0.00 |
| 1/80 | 4.80 | 4.80 | 0.00 |
| 1/160 | 4.80 | 4.80 | 0.00 |
| 1/320 | 4.80 | 4.30 | 0.00 |
| 1/640 | 4.30 | 4.80 | 0.00 |
| Citrate Buffer | 4.80 | 2.80 | 2.00 |

TABLE 22

The residual virus titres and log reductions of infectious B/Guangdong/120/00 virus after the 1-minute termination time point at different dilutions.

| | B/Guangdong | 1 Minute Incubation | |
|---|---|---|---|
| Dilution | Virus Titre (-log 10 TCID50) | Residual Influenza titre (-log 10 TCID50) | Virus log reductions (-log 10 TCID50) |
| 1/10 | 3.30 | 1.30 | 2.00 |
| 1/20 | 3.30 | 1.80 | 1.50 |
| 1/40 | 3.30 | 2.80 | 0.50 |
| 1/80 | 3.30 | 2.80 | 0.50 |
| 1/160 | 3.30 | 2.80 | 0.50 |
| 1/320 | 3.30 | 2.80 | 0.50 |
| 1/640 | 3.30 | 2.30 | 0.50 |
| Citrate Buffer | 3.30 | 0.00 | 3.30 |

TABLE 23

The residual virus titres and tog reductions of infectious B/Guangdong/120/00 virus after the 2-minute termination time point at different dilutions.

| | B/Guangdong | 2 Minute Incubation | |
|---|---|---|---|
| Dilution | Virus Titre (-log 10 TCID50) | Residual Influenza titre (-log 10 TCID50) | Virus log reductions (-log 10 TCID50) |
| 1/10 | 3.30 | 1.80 | 1.50 |
| 1/20 | 3.30 | 1.80 | 1.50 |
| 1/40 | 3.30 | 2.80 | 0.50 |
| 1/80 | 3.30 | 2.80 | 0.50 |
| 1/160 | 3.30 | 2.80 | 0.50 |
| 1/320 | 3.30 | 2.80 | 0.50 |
| 1/640 | 3.30 | 2.80 | 0.50 |
| Citrate Buffer | 3.30 | 0.00 | 3.30 |

TABLE 24

The residual virus titres and log reductions of infectious B/Guangdong/120/00 virus after the 5-minute termination time point at different dilutions.

| | B/Guangdong | 5 Minute Incubation | |
|---|---|---|---|
| Dilution | Virus Titre (-log 10 TCID50) | Residual Influenza titre (-log 10 TCID50) | Virus log reductions (-log 10 TCID50) |
| 1/10 | 3.30 | 1.30 | 1.50 |
| 1/20 | 3.30 | 1.30 | 1.50 |
| 1/40 | 3.30 | 2.80 | 0.50 |
| 1/30 | 3 30 | 2.80 | 0.50 |
| 1/160 | 3.30 | 2.80 | 0.50 |
| 1/320 | 3.30 | 3.30 | 0.00 |
| 1/640 | 3.30 | 1.80 | 1.50 |
| Citrate Buffer | 3.30 | 0.00 | 3.30 |

In the viricidal assay, a known titre of Influenza virus was used as the virus control; this control underwent the same procedures as the test compound, QR-435. The Influenza titre on all plates was consistent with a virus control titre greater than 2.5 (−log 10 TCID50).

EXAMPLE 8

In Vivo Testing of Anti-microbial Spray

Five minutes before being infected with an influenza virus of the strain A/Sydney/5/97 (H3N2), four groups of six naïve ferrets received intranasal doses of experimental or control compositions. The negative control group received a 15 phosphate buffer solution (PBS) placebo. The positive control group was treated with Tamiflu™ (oseltamivir phosphate, available from Roche Laboratories of Nutley, N.J.). One experimental group was treated with the nasal spray of Example 6, and the other was treated with a similar nasal spray that did not include green tea extract. After the initial challenge, the ferrets were dosed with their assigned composition twice a day.

The ferrets in the PBS treated control group exhibited all the symptoms typical of ferrets infected with influenza A, including weight loss, fever, increased inflammatory cell counts, and virus shedding on the first day after infection. The ferrets in the Tamiflu™ treated control group experienced no weight loss, no virus shedding, a reduction in inflammatory cell count rise, and no febrile illness.

Both the test formulation of Example 6 and the similar nasal spray that did not include green tea extract provided a low-level intermediary reduction inflammatory cell count, prevented development of a febrile illness, and delayed virus shedding that may indicate virus suppression. Ferrets treated with nasal spray according to Example 6, however, also showed some lessening of weight loss. Ferrets treated with nasal spray according to Example 6 were more active than ferrets treated with the Tamiflu™.

Changes may be made in carrying out the methods and to the compositions of the invention above set forth above without departing from the spirit and scope of the invention. It is intended that all matter contained in the above description shall be interpreted as illustrative and not in a limiting sense. The scope of this invention is to be determined from the claims appended hereto.

What is claimed is:

1. A method for treatment of an influenza virus in a patient, comprising the step of administering to a patient infected with an influenza virus, an amount of a composition in a form selected from the group consisting of a tablet, a capsule, a lozenge, a troche, a candy, a chewing gum, a spray, a powder, a gel, an elixir, a syrup, a suspension, a solution, and a dental product comprising:

a first ingredient selected from the group consisting of ginger extract, ginger fluid extract, ginger powder extract, ginger powder, a ginger tincture, and mixtures thereof;

a second ingredient selected from the group consisting of green tea powder, green tea powder extract, green tea fluid extract, green tea extract, tinctures of green tea, and mixtures thereof;

a third ingredient selected from the group consisting of turmeric powder extract, turmeric fluid extract, turmeric extract, turmeric powder, a turmeric tincture, and mixtures thereof; and an acceptable carrier;

said composition being effective, when administered, to inhibit the influenza virus in the patient.

2. The method of claim 1, wherein the influenza virus is selected from the group consisting of influenza A/Moscow/10/99, influenza B/Guangdong/ 120/00, influenza A/New Caledonia/20/99, influenza A/Panama/2007/99, and influenza A/Sydney/5/97.

3. The method of claim 1, wherein the composition is administered in a form selected from the group consisting of a tablet, a capsule, a lozenge, a troche, a hard candy, and a dental product.

4. The method of claim 1, wherein the composition is administered as a nasal spray or as a throat spray.

5. The method of claim 1, wherein the first ingredient comprises ginger root powder; the second ingredient comprises green tea extract; and the third ingredient comprises turmeric extract.

6. The method of claim 1, wherein each gram of the composition contains about 5 mg to about 20 mg of green tea extract, about 30 mg to about 150 mg of ginger root powder, and about 5 mg to about 20 mg of turmeric powder extract.

7. The method of claim 1, wherein the composition further comprises resveratrol.

8. A method for the treatment of an influenza virus in a patient, comprising the step of administering to a patient infected with an influenza virus, an amount of an anti-microbial composition in a form selected from the group consisting of a tablet, a capsule, a lozenge, a troche, a candy, a chewing gum, a spray, a powder, a gel, an elixir, a syrup, a suspension, a solution, and a dental product, comprising:

turmeric extract;

ginger root powder;

a green tea extract; and an acceptable carrier;

wherein the ginger root powder, green tea extract and turmeric extract are present in the anti-microbial composition in an amount which, when combined, is effective to inhibit said influenza virus when administered to the patient.

9. The method of claim 8, wherein the anti-microbial composition further comprises resveratrol.

10. The method of claim 8, wherein each gram of the anti-microbial composition contains about 5 mg to about 20 mg of green tea extract, about 30 mg to about 150 mg of ginger root powder, and about 5 mg to about 20 mg of turmeric powder extract.

11. The method of claim 1, wherein the composition further comprises at least one ingredient selected from the group consisting of glycerin, ethanol, propylene glycol and mixtures thereof.

12. The method of claim 11, wherein the composition comprises ethanol.

13. The method of claim 8, wherein the anti-microbial composition further comprises at least one ingredient selected from the group consisting of glycerin, ethanol, propylene glycol and mixtures thereof.

14. The method of claim 13, wherein the anti-microbial composition comprises ethanol.

15. The method of claim 8, wherein the influenza virus is selected from the group consisting of influenza A/Moscow/10/99, influenza B/Guangdong/ 120/00, influenza A/New Caledonia/20/99, influenza A/Panama/2007/99, and influenza A/Sydney/5/97.

16. The method of claim 1, wherein the composition further comprises an ingredient selected from horseradish root and horseradish flavor.

17. The method of claim 8, wherein the composition further comprises an ingredient selected from horseradish root and horseradish flavor.

18. The method of claim 16, wherein the composition further comprises an ingredient selected from slippery elm bark and slippery elm bark extract.

19. The method of claim 17, wherein the composition further comprises an ingredient selected from slippery elm bark and slippery elm bark extract.

20. The method of claim 1, wherein the ingredient obtainable from ginger is selected from the group consisting of ginger powder extract and ginger fluid extract.

21. The method of claim 1, wherein the ingredient obtainable from green tea is selected from the group consisting of green tea powder extract and green tea fluid extract.

* * * * *